United States Patent [19]

Mariol

[11] Patent Number: 4,695,250
[45] Date of Patent: Sep. 22, 1987

[54] BREAKAWAY ORTHODONTIC FACE BOW APPLIANCE

[75] Inventor: James F. Mariol, Cincinnati, Ohio

[73] Assignee: Fairdale Orthodontic Company, Cincinnati, Ohio

[21] Appl. No.: 877,326

[22] Filed: Jun. 23, 1986

[51] Int. Cl.[4] .............................................. A61C 7/00
[52] U.S. Cl. ....................................................... 433/5
[58] Field of Search ............................................ 433/5

[56] References Cited

U.S. PATENT DOCUMENTS

| | | | |
|---|---|---|---|
| 1,752,619 | 4/1930 | Summerfeld | 24/625 |
| 2,452,796 | 11/1948 | Skibsted | 280/193 |
| 2,518,179 | 8/1950 | Quinby et al. | 24/131 R |
| 2,940,622 | 6/1960 | Kays | 14/515 |
| 3,230,621 | 1/1966 | Lindquist et al. | 433/5 |
| 3,311,978 | 4/1967 | Haas et al. | 433/5 |
| 3,314,151 | 4/1967 | Rubin | 433/5 |
| 3,439,387 | 4/1969 | Churches | 24/300 |
| 4,087,915 | 5/1978 | Andrews | 72/214 |
| 4,115,921 | 9/1978 | Armstrong | 433/5 |
| 4,155,161 | 5/1979 | Armstrong | 433/5 |
| 4,215,983 | 8/1980 | Frazier | 433/5 |
| 4,226,589 | 10/1980 | Klein | 433/5 |
| 4,238,188 | 12/1980 | Armstrong | 433/5 |
| 4,368,039 | 1/1983 | Armstrong | 433/5 |
| 4,402,669 | 9/1983 | Frazier | 433/5 |
| 4,416,625 | 11/1983 | Armstrong | 433/5 |
| 4,439,148 | 3/1984 | Haas | 433/5 |
| 4,445,853 | 5/1984 | Klein | 433/5 |
| 4,553,933 | 11/1985 | Armstrong | 433/5 |
| 4,553,934 | 11/1985 | Armstrong | 433/5 |

*Primary Examiner*—Robert Peshock
*Attorney, Agent, or Firm*—Wood, Herron & Evans

[57] ABSTRACT

An orthodontic appliance comprising a generally U-shaped wire face bow having rearwardly facing arms terminating in hooked ends, an elastic headband connected between opposite ends of the face bow for applying tension to the arms of the face bow, and a pair of plastic wire connectors, one of which is connected between one end of the headband and a corresponding end of the face bow. Each of the connectors is formed of a single molded plastic piece and shaped so as to make a snap-fit connection around the wire of one of the hooked ends of the face bow.

12 Claims, 4 Drawing Figures

BREAKAWAY ORTHODONTIC FACE BOW APPLIANCE

The present invention relates to orthodontic face bow appliances, and more particularly, to a face bow appliance with breakaway connectors for the prevention of snap-back injury to the patient.

In the practice of orthodontics there is employed a technique of externally applying positioning forces for the straightening of the teeth or jaw. The technique involves the use of a U-shaped wire inner bow or mouth bow which fits into the patient's mouth with its ends facing rearwardly and connected to the teeth on each side of the patient's mouth. The connection is usually made to the molars with the use of a molar band to which is connected a buccal tube into which the ends of the mouth bow are seated. Typically, the external force is provided by an elastic tension device such as a strap behind the patient's neck or head. The tension forces produced are communicated from these devices to the mouth bow through an outer wire bow frequently called a face bow. The face bow is also U-shaped and is fastened at its center through the patient's mouth to the center of the mouth bow. Tension exerted across the face bow by the elastic tension device pulls against the mouth bow and thrusts it into the patient's mouth and against the teeth to which the ends of the mouth bow are secured. It is this force that is desired by the orthodontist for the repositioning of the patient's teeth or jaw.

The orthodontic appliances of the type thus far described were at one time often wired in place in the patient's mouth. This is less commonly done today for the reason that injury to the patient and destruction of the orthodontic appliance is reduced by allowing the mouth bow to detach from the patient's teeth when pulled upon and to be withdrawn when pulled from the patient's mouth. In this way, injury to the teeth and the internal orthodontic work caused by an accidental or intentional pulling on the external face bow is reduced. The removability of the mouth bow also facilitates eating by the patient and aids in the maintenance of oral hygiene.

The removability of the mouth bow upon the application of tension to the outer face bow has resulted in a different sort of safety problem. Due to the elastic nature of the band device which holds the face bow onto the patient and exerts the tension which translates into the compressive forces applied through the mouth bow, an accidental or otherwise unexpected pulling on the face bow, an occurrence which is generally seen with children, can result in a dangerous snap-back. The snap-back can result in injury to the patient caused by punctures from the sharp ends of the mouth bow. These can occur in the patient's mouth or on the patient's face and in some cases have occurred to patients' eyes. Accordingly, it has been recognized that breakaway devices or snap-back preventing devices are valuable in protecting the patient from such injuries.

The prior art has seen the development of a number of specific designs or breakaway connectors and tension limiting mechanisms to avoid the snap-back problem. The developments have included the use of elastic headbands and springs, various metal clips and snaps, and a number of devices providing tension control and adjustability. Generally, the function of these devices has been to provide some spring or band or other elastic device to apply tension to the ends of the face bow through a strapping arrangement which runs behind the patient's neck or head. To the elastic device have been added either breakaway clips or fasteners which disconnect the face bow thus preventing it from snapping back if it is pulled or extended over the patient's face, or some tension limiting mechanism has been incorporated, or both a tension limiting and breakaway devices have been used together.

The evolution of the prior art has resulted in the development of safety devices for this purpose which have become increasingly complicated and expensive. In addition to the undesired expense, the introduction of complexity has only theoretically provided improved function. A problem with the complex devices has been that the patients find them more uncomfortable and less easy to correctly reattach and adjust once they are removed and thus, they are less likely to be used correctly.

It has been a principal objective of the present invention to provide an orthodontic appliance of the face bow type which is safe against injury from snap-back, which is simple to use and to reconnect, and which is of low cost.

It is a particular objective of the present invention to provide a breakaway orthodontic face bow appliance which provides a consistent force up to a breakaway point in a low cost head gear.

It is a further objective of the present invention to provide a breakaway orthodontic face bow device which is easy for the orthodontist or patient to insert in the mouth, which can be reconnected by the patient without a need to master a complicated connection and adjustment procedure, and which is comfortable for the patient to use.

The present invention combines an otherwise conventional orthodontic face bow appliance with a simple single-piece, molded plastic breakaway connector which is used as a connecting link on each side of the patient's face between the face bow and the headband. To this, tension is provided, in accordance with the present invention, by elastic means which are carried by the headband between the two breakaway connectors. Preferably, an elastic headband made of an elastic fabric is employed.

In accordance with the preferred embodiment of the invention, the single-piece, molded plastic connectors are preferably C-shaped and form the breakaway connection by dipping onto hooks, preferably hooks formed in the ends of the face bow wire. With a headband of an elastic fabric, the simplest and most economical design of the present invention is to attach the molded plastic, C-shaped connectors to this material by insertion of the fabric bands in slots near the centers of the C-shaped plastic connectors.

The single molded plastic piece connector in this combination provides several advantages over the prior art. This connector results in a more positive acting and more reliable breakaway joint than the breakaway connectors developed by the prior art. This is found to be particularly advantageous with a design of the single piece, molded plastic external clip forming a breakaway connection around the internal piece formed of a hooked wire which the preferred embodiment of the present invention employs. In accordance with the present invention, the device provided is of far greater simplicity than devices of the prior art and provides at the same time durability and dependability. The present invention further provides great serviceability, comfort and usability by the patient. This particular combination of advantages is not provided by the devices of the prior art.

These and other objectives and advantages of the present invention will be more readily apparent from the following detailed description of the drawings in which.

Figure 1:
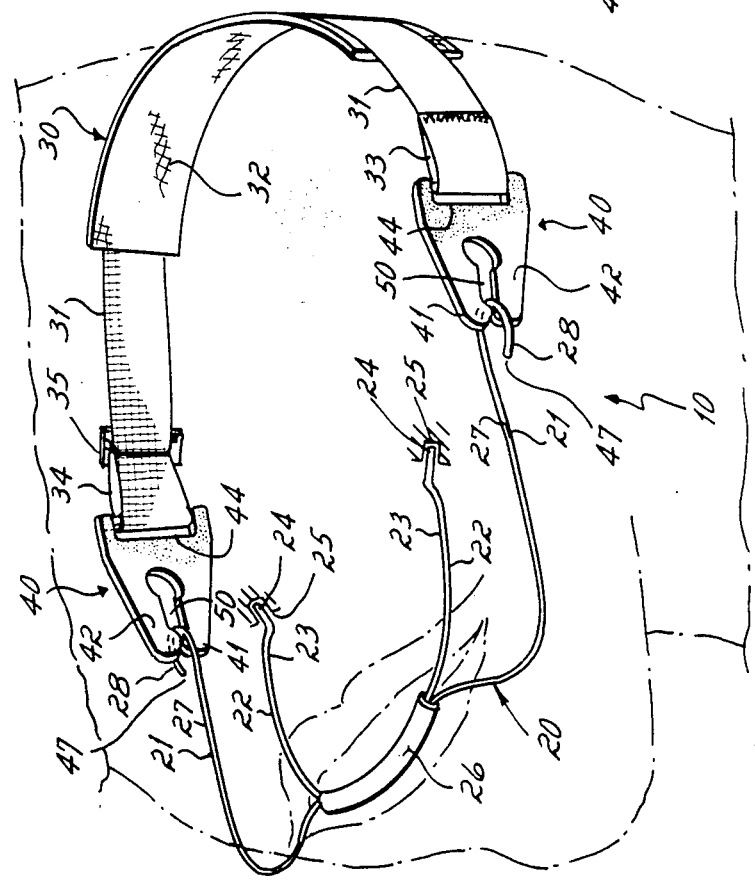
FIG. 1 is a diagrammatic view of the orthodontic face bow appliance employing the breakaway features as provided by the preferred embodiment of the present invention.

Referring to FIG. 1, an orthodontic appliance 10 according to the preferred embodiment of the present invention is shown. The appliance 10 includes a conventional orthodontic face bow assembly 20, an elastic headband 30, and a pair of breakaway connectors 40.

The face bow assembly 20 is formed of two U-shaped wire components usually of a stainless corrosion-resistant wire. These components are an outer bow or face bow 21 and an inner bow or mouth bow 22. The mouth bow 22 is the portion of the device which directly operates to perform the orthodontic function of positioning the patient's jaw or teeth. The mouth bow 22 is formed of a generally U-shaped wire and includes two rearwardly projecting arms 23 which terminate in free wire ends 24. The free ends 24 are typically fitted into pockets or buccal tubes which are secured by bands to the patient's molars. These are represented in FIG. 1 diagrammatically at 25. The corrective orthodontic force which is applied by the mouth bow 22 is a compressive force directed through the wire ends 24 of the mouth bow 22 against the points of attachment 25. It is this compressive force which also holds the mouth bow 22 in place against the attachment points 25. Protection against undesired tension forces at the points 25 is provided by allowing the ends 24 of the mouth bow 22 to be withdrawn freely from the attachment points 25 if pulled forwardly. This form of attachment also allows easy removal of the appliance by the patient who typically will not wear the appliance continuously, but often only at night. If the patient does wear the appliance 10 for longer periods, the appliance thus connected can be removed easily while the patient is eating or cleaning his teeth.

The mouth bow 22 is connected at its center to the wire U-shaped outer bow or face bow 21 through a band or other bonding means 26. The face bow 21 extends around the outside of the patient's face and includes a pair of rearwardly facing arms 27 extending from the center connection point 26 and terminating in a pair of hooked ends 28 integrally formed of the wire of the face bow 21.

When in use, the wire of the mouth bow 22 is maintained in constant compression along its length to exert force against the tooth attachment points 25. The compressive force is maintained in the mouth bow by force directed rearwardly against the mouth bow at its point of attachment 26 through the application of constant tension force in the face bow 21.

Around the rear of the patient's head is provided what will be generically referred to here as a "headband" 30. A headband may be in the form of a neckband around the base of the patient's skull at the neck or may be in the form of a head cap which sits higher on the patient's head. The specific type of headband is determined by the nature of the orthodontic forces which the orthodontist desires to apply and the orthodontic result he is trying to achieve. Frequently, multiple straps will form this headband.

At some point between its ends, the headband 30 is provided with an elastic element in some form which generates a reactive tension force when stretched. This originates the tension force, which is in turn applied by the headband 30 across the face bow 21. Many devices of the prior art use springs for this function. Others use elastic fabric straps, which is the embodiment preferred in the present invention. In any event, the headband 30 includes a strap 31, in this case a strap of elastic fabric material, to which is sewn at its center a pad 32 which distributes the force against the rear of the patient's head to provide comfort. The strap 31 is sewn at one end into a loop 33 and formed at its other end into a loop 34, but with the loop 34 being adjustable by means of a conventional buckle 35. The loops 33 and 34 are attached to breakaway connectors 40. The connectors 40 are in turn slipped onto the hooked ends 28 of the face bow 21 for breakaway release upon application of excessive tension forces.

In use, the tension is adjusted in the elastic strap 31 of the headband 30 through the setting of the buckle 35. This tension thus applied is directed through the connectors 40 and to the hooked ends 28 of the face bow 21, thus applying a tension in the wire of the face bow 21 and directing therewith an inward force at the center connection 26 to the mouth bow 22. This applies the desired corrective compressive force at the tooth attachment points 25 in the mouth of the patient and also serves to retain the assembly 20 against the patient's mouth.

Figure 2:
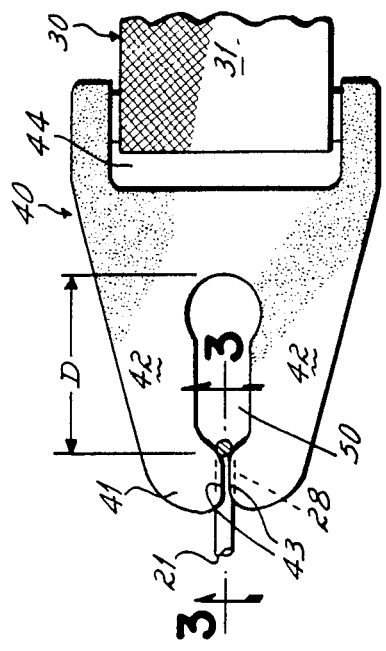
FIG. 2 is a side view of one of the molded plastic breakaway connectors in accordance with the illustrated embodiment of the present invention showing its connection to a wire hook formed in the end of the orthodontic face bow.

Referring to FIG. 2, the details of the breakaway connector 40 and its manner of attachment in the appliance 10 is illustrated in more detail. The connector 40, according to the present invention, is formed of a single molded plastic piece. THis piece is generally symmetrical and C-shaped. It includes a slotted end 41 formed by the opposing tips of the C-shaped piece, adapted to receive a wire hook which is, in this case, the hooked end 28 of the face bow 21. The slot 50 of the slotted end 41 is defined by a pair of opposed arms 42. The tips 43 of the arms 42 are in very close proximity to each other. In an unstressed condition, the distance between the tips 43 of the arms 42 will be less than the thickness of the wire of which the hooked ends 28 of the face bow 21 are formed. This relationship defines the breakaway tension at which the disconnection will occur as explained more fully below. When a hooked end 28 is inserted in the slot 50, the connection between the hooked end 28 and the connector 40 will support tension up to some predesigned limit.

The center portion of the C-shaped connector 40 is provided with a slot 44. The purpose of the slot 44 is to provide a simple and efficient means for attachment of the strap 31 of the headband 30. The strap 31 is simply located through the slot 44 at the loops 33 and 34 found in the ends of the strap 31. Tension applied to the connector by the elastic strap 31 is transmitted through the connector 40 and to the hooked end 28 of the face bow 21.

Figure 3:
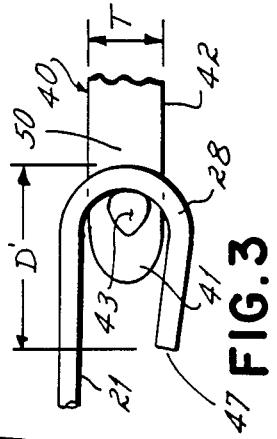
FIG. 3 is a sectional view along line 3—3 of FIG. 2 showing the engagement of the wire hook by an arm of the molded plastic connector.

The manner in which the hooked end 28 is retained to the connector 40 is better illustrated by reference to FIG. 3. In FIG. 3, the hooked end 28 of the face bow 21 is shown inserted in the slot 50 of the connector 40. In FIG. 3, the position of the one of the arms 42 is shown with the tip of the arm 43 shown in contact with the hook 28. The tip 43 as outlined in FIG. 3 represents the portion of the arm 42 which lies in the path of the hook 28, permitting communication of the tension force to the face bow 21 and preventing the hook 28 from withdrawing from the slot 50 when the tension forces are within tolerable limits.

Figure 4:
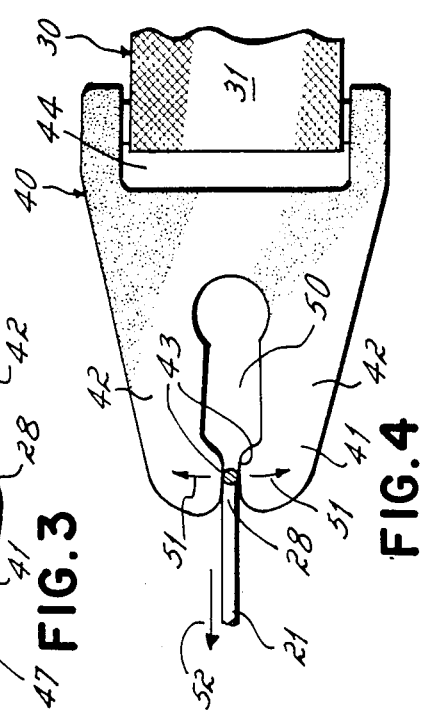
FIG. 4 is a view similar to that of FIG. 2 showing the outward elastic displacement of the arms of the plastic connector during the course of the breakaway action which results when excess tension is applied between the connector and the hook, and showing how the hook disengages from the connector in the breakaway process.

The breakaway feature of the connector 40 is better illustrated by reference to FIG. 4. It has been found that a suitable connector for this purpose is one molded of a single Delrin plastic piece. In FIG. 4, the slot 50 surrounded by the arms 42 is shown. The arms 42 are resilient and resistant to outward motion, in the direction illustrated by the arrows 51 of the tips 43. This outward displacement of the tips 43 will occur when the hook 28 is subjected to a tension force which causes it to move in the direction of the arrow 52 in relation to the connector 40 to thereby cause the tips 43 to separate in the direction of the arrows 51. In practice, the greater the tension between the hook 28 and the connector 40, the greater the displacement of the hook between the tips 43 will become and the greater the separation in the direction 51. This movement is resisted by the reactive force on the tips 43 caused by the resiliency of the molded plastic arms 42. At the point where the tips 43 are separated by the diameter of the wire 28, a specific reactive force between the tips 43 and the wire of the hook 28 is achieved. At this point, the force resisting the tension between the hook 28 and the connector 40 is the friction force between the plastic tips 43 and the wire of the hook 28. This is the breakaway tension of the connector. Where the tension exceeds that force, a breakaway of the connection occurs.

The movement of the hook 28 from the slot 41 of the connector 40 is accompanied by a forward movement of the connector 40 due to the elasticity applied by the strap 31 of the headband 30. The dimensioning of the connector 40 in relation to the wire of the hook 28 defines a threshold tension at which the breakaway will occur. The forward displacement of the connector 40 against the elasticity of the straps 31 is a function of this breakaway tension force. Thus, the breakaway connection which is provided will very effectively, dependably and simply limit the amount of snap-back that can occur if the face bow should be pulled forward an excessive amount.

Reversing the disconnection process, the connector 40 can be very easily reconnected to the hook 28. This is done by merely inserting the hook 28 into the connector slot 50 and then moving it forwardly against the tips 43 of the arms 42. The distance between the end 47 and the shank of the wire hook 28 is greater than the thickness T of the connector 40, and the depth D of the slot 50 is greater than the depth D' of the hook 28 so that the hook 28 may be easily inserted into the slot 50 and then moved forwardly in the slot until the tip 43 of the connector engages the wire of the hook 28. This connection can very easily be done or undone by the patient without having to overcome the snap-fit connector between the tips 43 of the connector and the hook 28.

The simplicity and economy of the overall construction of the orthodontic appliance 10 according to the present invention and particularly, the preferred embodiment of the present invention which is illustrated, and the accompanying durability, dependability, and ease of use for the patient, provides safety against injury in the nature of puncture wounds caused by snap-back of the mouth bow with a substantial combination of advantages not heretofore experienced with the prior art.

From some specific purposes, while it may be desirable to introduce additional elements of complexity into structures for appliances of the type shown without fully departing from the principles of the present invention, it will be appreciated by those skilled in the art that the breakaway connection between the single-piece, molded plastic connector and hook in an orthodontic appliance of the type described can nonetheless by employed retaining the advantages provided by the present invention.

Having described the invention, what is claimed is:

1. An orthodontic appliance comprising:
   a generally U-shaped wire face bow having rearwardly facing arms terminating in hooked ends integrally formed of the wire,
   an elastic headband connected between the opposite ends of said face bow for applying tension to the arms of said face bow,
   a pair of breakaway connectors, each connected between an opposite one of the ends of said headband and a corresponding opposite one of the ends of said face bow such that said breakaway connectors are the only elements making the connection between the headband and the hooked ends of said face bow, and
   each of said connectors being formed of a single molded plastic piece and shaped so as to make a snap-fit connection around the wire of one of said hooked ends.

2. The orthodontic appliance of claim 1 wherein said breakaway connectors are generally C-shaped.

3. The orthodontic appliance of claim 2 wherein said breakaway connectors each has a slot therein near the center thereof for connection to one of the ends of said headband.

4. The orthodontic appliance of claim 1 wherein said breakaway connectors each has a pair of elastic opposed arms extending around one of said hooked ends of said face bow for holding said connector in engagement with said hooked end when subjected to tension below a threshold limit and for disengaging said connector from said hooked end when subjected to tension above said threshold limit.

5. An orthodontic appliance comprising:
   a face bow,
   a headband connected between the opposite ends of said face bow and including elastic means for applying tension at the ends thereof,
   a pair of breakaway connectors, one connected at each end of said headband between said headband and the end of said face bow to form a breakaway connection between the respective connected ends such that said breakaway connectors are the only elements making the connection between the headband and the hooked ends of said face bow, each pair of connected ends including an end formed into a hook presenting an incompressible convex member to be engaged by said connector, and each of said connectors being formed of a single molded plastic piece and shaped so as to make a snap-fit connection around one of said hooks.

6. The orthodontic appliance of claim 5 wherein said elastic means of said headband includes a band of elastic fabric connected in series between the ends of said headband.

7. The orthodontic appliance of claim 5 wherein said breakaway connectors are generally C-shaped.

8. The orthodontic appliance of claim 7 wherein said breakaway connectors each has a slot near the center thereof for connection to one of the ends of said headband.

9. The orthodontic appliance of claim 5 wherein said breakaway connectors each has a pair of elastic opposed arms extending around one of said hooks for holding said connector in engagement with one of said hooks when subjected to tension below a threshold limit and for disengaging said connector from said one of said hooks when subjected to tension above said threshold limit.

10. The orthodontic appliance of claim 5 further comprising a generally U-shaped wire mouth bow connected at its center to the center of said face bow, and having rearwardly facing arms terminated in ends adapted to be held with pressure in contact against orthodontic braces, and wherein said connectors are adapted to be held in engagement with said hooks when subjected to tension up to a threshold limit and for disengaging said connectors from said hooks when subjected to tension above said threshold limit, the threshold limit being approximately the level of tension occurring at the point where said mouth bow is pulled out of engagement with said orthodontic braces.

11. An orthodontic appliance comprising:

a generally U-shaped wire face bow having rearwardly facing arms terminating in a pair of hooked ends integrally formed of the wire, each of said hooked ends having an end, a curve, and a shank spaced from said end, each of said hooked ends having a depth between said ends and the bottoms of said curves, an elastic headband connected between the opposite ends of said face bow for applying tension to the arms of said face bow, a pair of breakaway connectors, each connected between an opposite one of the ends of said headband and a corresponding opposite one of the ends of said face bow such that said breakaway connectors are the only elements making the connection between the headband and the hooked ends of said face bow, each of said connectors being formed of a single molded plastic piece and shaped so as to make a snap-fit connection around the wire of one of said hooked ends, each of said breakaway connectors having a pair of elastic opposed arms and a gap defined between tips of said arms, said opposed arms defining a slot extending away from said gap, said slot having a depth greater than the depth of said hooked ends of said wire, said connector having a thickness less than the space between said end of said hook and said shank so that said hooks may be inserted into said slots without the curve of said hooks having to pass through said gap defined between the tips of said arms, and said tips of said opposed arms being engageable with the curves of said hooks to hold said connectors in engagement with said hooks when subjected to tension below a threshold limit and to disengage said hooks when subjected to tension above said threshold limit.

12. An orthodontic appliance comprising:

a generally U-shaped wire face bow having rearwardly facing arms terminating in hooked ends integrally formed of the wire, an elastic headband having a pair of opposite ends connected between the ends of said face bow for applying tension to the arms of said face bow, and a pair of unitary breakaway connectors, one of said pair of unitary breakaway connectors being connected to each end of said headband and a corresponding of said face bow such that said unitary breakaway connectors are the only elements making the connections between the ends of said headband and the hooked ends of said face bow, each of said connectors being formed so as to make a snap-fit connection around the wire of one of said hooked ends of said wire face bow.

* * * * *